(12) United States Patent
Hisano et al.

(10) Patent No.: US 9,776,185 B2
(45) Date of Patent: Oct. 3, 2017

(54) REAGENT CONTAINER AND AUTOMATIC ANALYSIS APPARATUS

(71) Applicant: HITACHI HIGH-TECHNOLOGIES CORPORATION, Tokyo (JP)

(72) Inventors: Hidenori Hisano, Tokyo (JP); Hiroyuki Mishima, Tokyo (JP); Hiroshi Ohga, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 78 days.

(21) Appl. No.: 14/437,951

(22) PCT Filed: Oct. 25, 2013

(86) PCT No.: PCT/JP2013/079029
§ 371 (c)(1),
(2) Date: Apr. 23, 2015

(87) PCT Pub. No.: WO2014/069376
PCT Pub. Date: May 8, 2014

(65) Prior Publication Data
US 2015/0290645 A1 Oct. 15, 2015

(30) Foreign Application Priority Data
Oct. 30, 2012 (JP) .................... 2012-238919

(51) Int. Cl.
*B01L 3/00* (2006.01)
*G01N 35/10* (2006.01)
(Continued)

(52) U.S. Cl.
CPC .............. *B01L 3/523* (2013.01); *B65D 51/16* (2013.01); *G01N 35/1002* (2013.01);
(Continued)

(58) Field of Classification Search
CPC ......... B01L 2300/042; B01L 2300/048; B01L 3/523; B01L 2200/0684; B01L 2300/049; B65D 51/16
See application file for complete search history.

(56) References Cited

U.S. PATENT DOCUMENTS 5,635,137 A * 6/1997 Manz ...................... B01L 3/508
206/446
6,044,997 A * 4/2000 Ogg ...................... B65D 23/102
215/381

(Continued)

FOREIGN PATENT DOCUMENTS

| JP | 2005-83777 A | 3/2005 |
| JP | 2009-210274 A | 9/2009 |
| JP | 2009210274 A * | 9/2009 |

OTHER PUBLICATIONS

Chinese Office Action received in corresponding Chinese Application No. 201380055505.1 dated Jan. 28, 2016.

*Primary Examiner* — Sean E Conley
*Assistant Examiner* — Benjamin R Whatley
(74) *Attorney, Agent, or Firm* — Mattingly & Malur, PC

(57) ABSTRACT

A reagent container used in an automatic analysis apparatus capable of preventing reagent in the reagent container from spattering out of the reagent container even when the reagent container with large capacity is rotated at a high speed and an automatic analysis apparatus using the reagent container are provided. A reagent container 12 for an automatic analysis apparatus has a first opening 27 used for sucking reagent and a second opening 28 used for the filling of the reagent. The second opening 28 is provided with an attachable/detachable lid 29. The lid 29 is provided with an air vent 33, a first shield plate 30 and a second shield plate 31 for preventing spattering of the reagent through the air vent 33 due to a wave motion of the reagent.

9 Claims, 11 Drawing Sheets

(51) Int. Cl.
 *B65D 51/16* (2006.01)
 *G01N 35/04* (2006.01)

(52) U.S. Cl.
 CPC ..... *B01L 2200/06* (2013.01); *B01L 2200/141* (2013.01); *B01L 2300/021* (2013.01); *B01L 2300/042* (2013.01); *B01L 2300/046* (2013.01); *B01L 2300/048* (2013.01); *B01L 2300/049* (2013.01); *G01N 2035/0453* (2013.01)

(56) References Cited

U.S. PATENT DOCUMENTS

| | | | | |
|---|---|---|---|---|
| 6,050,435 | A * | 4/2000 | Bush | B65D 47/2031 215/249 |
| 6,193,933 | B1 * | 2/2001 | Sasaki | G01N 35/00663 422/537 |
| 8,231,027 | B2 * | 7/2012 | Wang | A01N 43/16 141/65 |
| 8,702,949 | B2 * | 4/2014 | Ohura | G01N 27/44743 204/451 |
| 2002/0179615 | A1 * | 12/2002 | Hakim | A47G 19/2272 220/714 |
| 2005/0183774 | A1 * | 8/2005 | Kitagawa | B01L 3/0293 137/399 |
| 2005/0247715 | A1 * | 11/2005 | Ellsworth | A61M 1/3693 220/501 |
| 2007/0077655 | A1 * | 4/2007 | Unger | C12M 99/00 435/404 |
| 2007/0102393 | A1 * | 5/2007 | Colin | B01L 3/50825 215/249 |
| 2007/0134134 | A1 * | 6/2007 | Watts | A61B 10/0096 600/573 |
| 2008/0014629 | A1 * | 1/2008 | Klein | B01L 3/50853 435/287.1 |
| 2008/0240986 | A1 * | 10/2008 | Chang | A61B 10/007 422/68.1 |
| 2009/0145754 | A1 * | 6/2009 | Yang | G01N 33/5438 204/403.02 |
| 2010/0015009 | A1 * | 1/2010 | Wallace | B01L 3/0268 422/400 |
| 2015/0203258 | A1 * | 7/2015 | Staton | C12M 23/04 220/371 |

\* cited by examiner (a)

(b)

(a)

(b)

(a)

(b)

REAGENT CONTAINER AND AUTOMATIC ANALYSIS APPARATUS

TECHNICAL FIELD

The present invention relates to a technique of an automatic analysis apparatus, and particularly relates to a technique effectively applied to a reagent container used for an automatic analysis apparatus and an automatic analysis apparatus using the reagent container.

BACKGROUND ART

In a conventional automatic analysis apparatus, a sample such as taken serum or urine (also referred to as specimen, test liquid or the like) and reagents in accordance with test items are respectively dispensed into reaction containers, and reaction of liquid to be tested is measured. Identification labels are attached to reagent containers so as to identify a plurality of test reagents.

A plurality of the reagent containers can be stored in a reagent storage cabinet, and reagents necessary for analysis are arranged on a rotary table while being contained in the reagent containers, and are moved to a predetermined place when a test is requested. Since the amount of test reagent to be used and the frequency of test vary in accordance with the test items, the amount of reagent necessary for one day varies. In order to avoid a trouble of frequent replacement of reagent containers, capacities of the reagent containers are changed in accordance with the test items, and the reagent container with a large capacity is used for a test item that requires a large amount of the reagent to be used.

As a technique of the automatic analysis apparatus described above, for example, Patent Document 1 describes a technique relating to a reagent container. The reagent container described in Patent Document 1 has a structure including a reagent outlet with a reagent dispensing probe and a cylindrical member inserted into the reagent outlet.

RELATED ART DOCUMENTS

Patent Documents

PATENT DOCUMENT 1: Japanese Patent Application Laid-Open Publication No. 2005-83777

SUMMARY OF THE INVENTION

Problems to be Solved by the Invention

As a result of the studies on the conventional automatic analysis apparatuses including Patent Document 1 by the inventors of the present invention, the following has been revealed.

In recent years, since the automatic analysis apparatus has been sped up and the number of specimens to be processed has increased, the amount of reagent necessary for one day has also increased, so that the reagent container with a capacity larger than that of the reagent container described in Patent Document 1 has been required. Due to the speeding-up of the automatic analysis apparatus, a reagent disc also rotates and stops at a high speed, and a centrifugal force to the reagent also increases. As a result, the increase in the centrifugal force and impact at the stop together with the increase in capacity of the reagent container causes large oscillation of the reagent, and the oscillation of the reagent sometimes causes spattering of the reagent in the reagent container to the outside of the reagent container. The spattering of the reagent stains the identification label of the reagent container or a window through which the identification label is read, and this may result in the case where the analysis result cannot be acquired.

Thus, in view of the problem mentioned above, an object of the present invention is to provide a reagent container used for an automatic analysis apparatus capable of preventing reagent in the reagent container from spattering out of the reagent container even when the reagent container with large capacity is rotated at a high speed, and an automatic analysis apparatus using the reagent container.

The above and other objects and novel characteristics of the present invention will be apparent from the description of the present specification and the accompanying drawings.

Means for Solving the Problems

The following is a brief description of an outline of the typical invention disclosed in the present application.

Specifically, a typical reagent container is a reagent container for an automatic analysis apparatus, and it has following characteristics. The reagent container includes: a first opening used for sucking reagent; and a second opening used for filling the reagent container with the reagent. The second opening is provided with an attachable/detachable lid. The lid is provided with an air vent and a shield plate for preventing spattering of the reagent through the air vent due to a wave motion of the reagent.

Also, the air vent is desirably a hole having an area that is not less than or the same as an area of the first opening.

Also, a typical automatic analysis apparatus is an automatic analysis apparatus using the reagent container, and it has following characteristics. The automatic analysis apparatus includes: a reagent disc on which a plurality of the reagent containers are placed; a reaction container for making the reagent in the reagent container react with a specimen to be analyzed; and a reagent dispensing probe for sucking the reagent from the reagent container on the reagent disc and dispensing the reagent into the reaction container.

Effect of the Invention

The effects obtained by typical embodiments of the invention disclosed in the present application will be briefly described below.

Namely, as a representative effect, even when a reagent container with large capacity is rotated at a high speed, reagent in the reagent container can be prevented from spattering out of the reagent container. Therefore, an identification label of the reagent container and a window through which the identification label is read can be prevented from being stained. As a result, a reading failure of a bar code of the identification label due to the spattering of the reagent can be reduced, and the automatic analysis apparatus with high reliability can be provided.

BRIEF DESCRIPTIONS OF THE DRAWINGS

Figure 16:
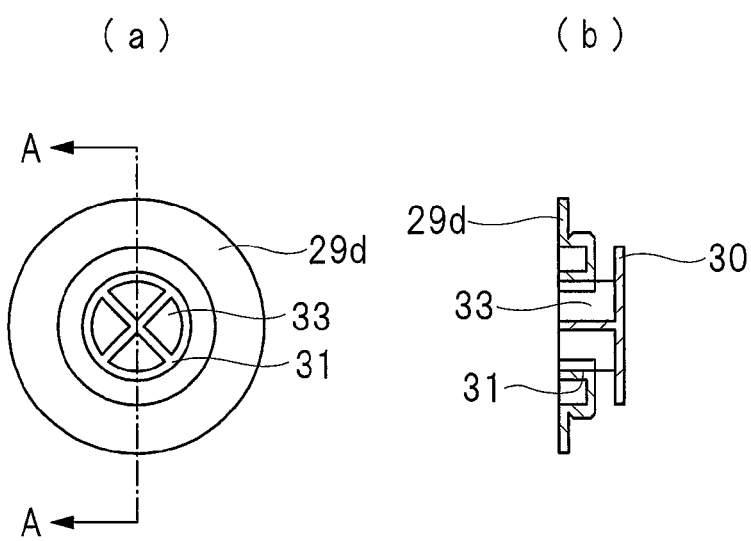
Figure 17:
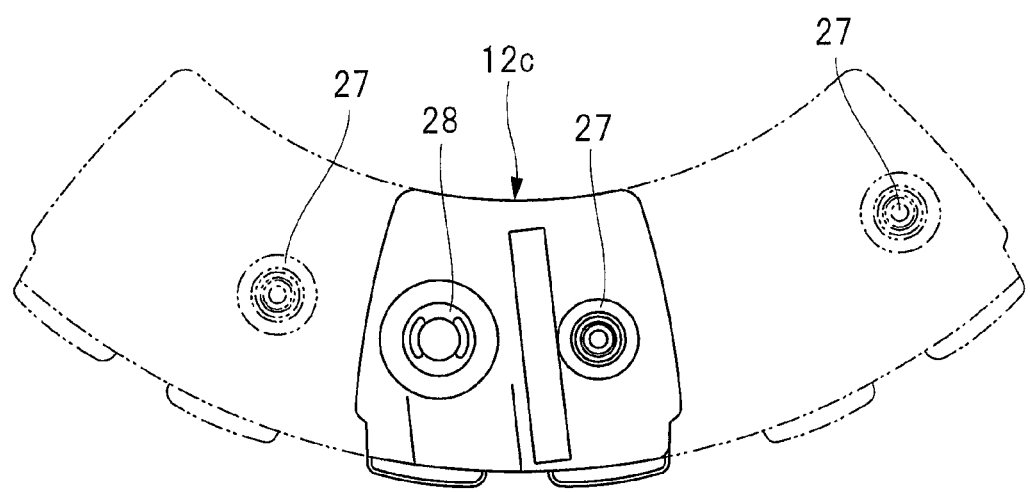

FIG. 16 is a diagram for describing one example (Example 4) of a configuration of the lid of the reagent container used in the automatic analysis apparatus according to the fourth embodiment of the present invention, (a) is a plan view, and (b) is a cross-sectional view taken along the line A-A of (a); and FIG. 17 is a plan view for describing one example of a configuration of a reagent container used in an automatic analysis apparatus according to the fifth embodiment of the present invention.

DETAILED DESCRIPTION OF EMBODIMENT

In the embodiments described below, the invention will be described in a plurality of sections or embodiments when required as a matter of convenience. However, these sections or embodiments are not irrelevant to each other unless otherwise stated, and the one relates to the entire or a part of the other as a modification example, details, or a supplementary explanation thereof. Also, in the embodiments described below, when referring to the number of elements (including number of pieces, values, amount, range, and the like), the number of the elements is not limited to a specific number unless otherwise stated or except the case where the number is apparently limited to a specific number in principle, and the number larger or smaller than the specified number is also applicable.

Further, in the embodiments described below, it goes without saying that the components (including element steps) are not always indispensable unless otherwise stated or except the case where the components are apparently indispensable in principle. Similarly, in the embodiments described below, when the shape of the components, positional relation thereof, and the like are mentioned, the substantially approximate and similar shapes and the like are included therein unless otherwise stated or except the case where it is conceivable that they are apparently excluded in principle. The same goes for the numerical value and the range described above.

Summary of Embodiments

A reagent container according to the present embodiments is a reagent container for an automatic analysis apparatus, and it has the following characteristics (as one example, reference characters of corresponding components are given in parentheses). The reagent container has a first opening (27) used at a time of sucking reagent and a second opening (28) used for filling the reagent container with reagent. The second opening is provided with an attachable/detachable lid (29). The lid is provided with an air vent (33) and shield plates (30, 31, 34 and 35) for preventing spattering of the reagent through the air vent due to a wave motion of the reagent.

Further, the automatic analysis apparatus according to the present embodiments is an automatic analysis apparatus using the above-described reagent container, and it has the following characteristics (as one example, reference characters of corresponding components are given in parentheses). The automatic analysis apparatus has a reagent disc (26) on which a plurality of reagent containers are placed, a reaction container (6) for making the reagent in the reagent container react with a specimen to be analyzed, and a reagent dispensing probe (8) for sucking the reagent from the reagent container on the reagent disc and dispensing the reagent into the reaction container.

The respective embodiments based on the summary of the embodiments described above will be described in detail below with reference to the drawings. Note that the same components are denoted by the same reference characters throughout the drawings for describing the embodiments, and the repetitive description thereof is omitted.

First Embodiment

An automatic analysis apparatus using a reagent container according to the first embodiment will be described with reference to FIG. 1 to FIG. 10.

<Configuration and Operation of Automatic Analysis Apparatus>

Figure 1:
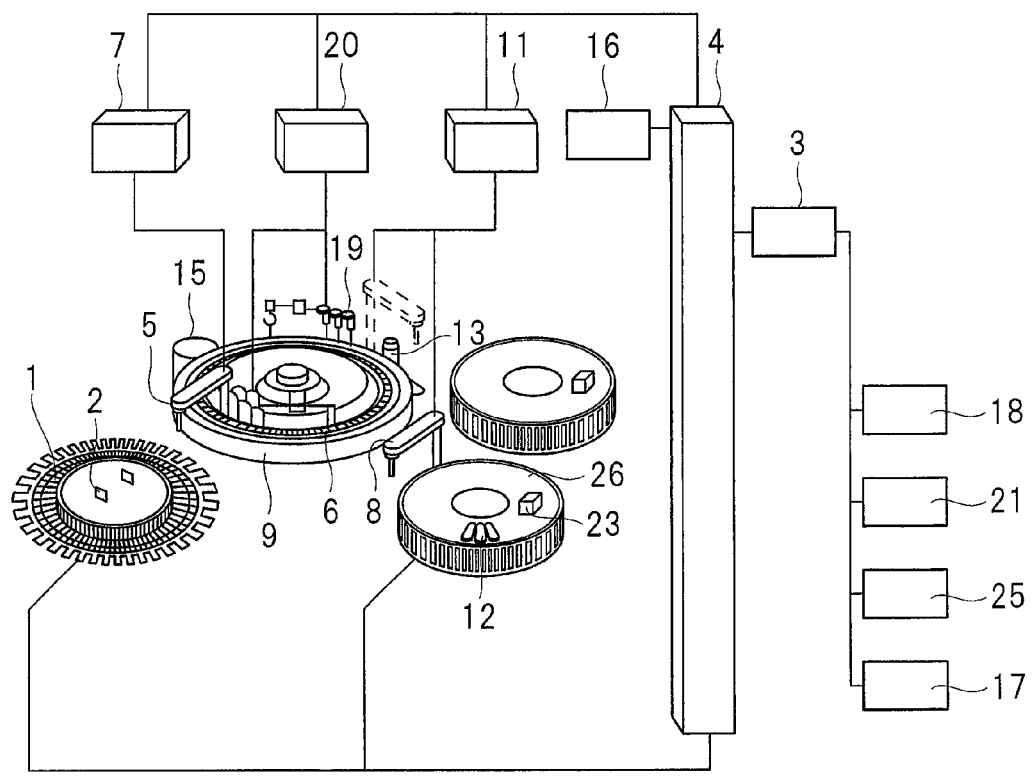
FIG. 1 is a schematic diagram for describing one example of a configuration and an operation of an automatic analysis apparatus according to the first embodiment of the present invention.

A configuration and an operation of the automatic analysis apparatus according to this embodiment will be described with reference to FIG. 1. FIG. 1 is a schematic diagram for describing one example of the configuration and the operation of the automatic analysis apparatus.

In FIG. 1, 1 denotes a specimen container, 2 denotes a specimen disc, 3 denotes a computer, 4 denotes an interface, 5 denotes a specimen dispensing probe, 6 denotes a reaction container, 7 denotes a specimen pump, 8 denotes a reagent dispensing probe, 9 denotes a reaction tank, 11 denotes a reagent pump, 12 denotes a reagent container, 13 denotes an agitating mechanism, 15 denotes a multi-wavelength photometer, 16 denotes an A/D converter, 17 denotes a printer, 18 denotes a CRT, 19 denotes a cleaning mechanism, 20 denotes a cleaning mechanism vacuum pump, 21 denotes a keyboard, 23 denotes a reagent bar code reading device, 25 denotes a hard disc, and 26 denotes a reagent disc.

The automatic analysis apparatus according to this embodiment is configured to mainly include the specimen disc 2 on which the plurality of specimen containers 1 are placed, the reagent disc 26 on which the plurality of the reagent containers 12 are placed, the reaction tank 9 in which the plurality of the reaction containers 6 are placed, the specimen dispensing probe 5 disposed near the specimen disc 2 and the reaction tank 9, the reagent dispensing probe 8 disposed near the reagent disc 26 and the reaction tank 9, the agitating mechanism 13 disposed near the reaction tank 9, the multi-wavelength photometer 15, and the cleaning mechanism 19.

The specimen disc 2 is made up of a circular rotating disc, and the plurality of specimen containers 1 containing specimens to be analyzed are placed on a circumference of the rotating disc. A specimen dispensing mechanism including the specimen dispensing probe 5 is disposed near the specimen disc 2. The specimen dispensing probe 5 sucks a specimen from the corresponding specimen container 1 and discharges this specimen to the corresponding reaction container 6. The specimen pump 7 is connected to the specimen dispensing probe 5, and the specimen pump 7 dispenses a predetermined amount of specimen into the reaction container 6.

The reagent disc 26 is made up of a circular rotating disc, and the plurality of the reagent containers 12 containing specimens are arranged on the circumference of the rotating disc. A reagent dispensing mechanism including the reagent dispensing probe 8 is disposed near the reagent disc 26. The reagent dispensing probe 8 sucks the reagent from the corresponding reagent container 12 and discharges the reagent to the corresponding reaction container 6. The reagent pump 11 is connected to the reagent dispensing probe 8, and the reagent pump 11 dispenses a predetermined amount of the reagent into the reaction container 6.

A plurality of reaction container holders which hold the plurality of the reaction containers 6 in which specimens and reagents are dispensed are arranged on a circumference of the reaction tank 9. The reaction disc on which the reaction container holders for holding the reaction containers 6 are arranged can be intermittently rotated by a driving mechanism. Further, the agitating mechanism 13, the multi-wavelength photometer 15, the cleaning mechanism 19 and the like are disposed near the reaction disc.

The agitating mechanism 13 is a mechanism for agitating contents (specimens and reagents) in the reaction containers 6. The multi-wavelength photometer 15 is a mechanism for measuring absorbance of the contents in the reaction containers 6. The cleaning mechanism 19 is a mechanism for cleaning inside of the reaction containers 6. The cleaning mechanism vacuum pump 20 is connected to the cleaning mechanism 19, and a cleaning solution is supplied by the cleaning mechanism vacuum pump 20.

The specimen disc 2 of the specimen containers 1, the reagent disc 26 of the reagent containers 12, the reaction disc of the reaction containers 6, the specimen dispensing mechanism, the reagent dispensing mechanism, the agitating mechanism 13, the multi-wavelength photometer 15, the cleaning mechanism 19 and the like are connected to the computer 3 via the interface 4, so that respective operations thereof are controlled.

A display device such as the CRT 18, an input device such as the keyboard 21, a storage device such as the hard disc 25, an output device such as the printer 17 and others are connected to a main body of the computer 3 including, for example, an arithmetic processing function and a storage function.

For example, analysis parameters, the analyzable number of times of each reagent container, the maximum analyzable number of times, a calibration result, and an analyzed result are stored in the hard disc 25. The analysis parameters include item codes allocated to measurement items, measurement wavelengths, specimen dispensing amounts, calibration methods, standard solution concentration, the number of standard solutions, check values for analysis abnormality, and the reagent container codes necessary for the respective measurement items.

Further, each of the reagent bar codes stuck to the reagent containers 12 has a manufacturing lot number of reagent, a container size, an expiration date of reagent, a sequence number and the like as reagent information. The sequence numbers are numbers different for each of the containers, and enable the identification of the respective reagent containers 12.

In a method for registering the reagent containers 12, the reagent container 12 is first set on the reagent disc 26 of an analyzing unit. Then, when the execution of reading of the reagent information is input, the reagent disc 26 starts to rotate, and the reagent bar code reading device 23 reads the reagent bar code during the rotation. The computer 3 searches the registered items of the analysis parameters for a corresponding measurement item with using the reagent container code included in the information of the read reagent bar code as a key, and stores the reagent information for each of the reagent containers in the hard disc 25.

In the automatic analysis apparatus according to this embodiment, the specimen analyzing operation is executed in the order of sampling, reagent dispensing, agitation, photometric measurement, cleaning of the reaction containers and data processing such as concentration conversion as described below.

The plurality of specimen containers 1 containing specimens are placed on a rack. This rack is controlled by the computer 3 via the interface 4.

First, the rack on which the plurality of specimen containers 1 containing the specimens are placed is moved below the specimen dispensing probe 5 in accordance with an analyzing order of the specimens, and a predetermined amount of the specimen of the predetermined specimen container 1 is dispensed into the reaction container 6 by the specimen pump 7 connected to the specimen dispensing probe 5.

Further, the reaction container 6 into which the specimen is dispensed is moved to a first reagent adding position in the reaction tank 9. A predetermined amount of first reagent sucked from the reagent container 12 is added to the moved reaction container 6 by the reagent pump 11 connected to the reagent dispensing probe 8.

Subsequently, the reaction container 6 after the addition of the first reagent is moved to a position of the agitating mechanism 13, and first agitation is carried out. Such addition and agitation of the reagent are performed for the first to fourth reagents.

Further, the reaction container 6 whose contents have been agitated passes through light flux emitted from a light source, and the absorbance at this time is detected by the multi-wavelength photometer 15. A detected absorbance signal enters the computer 3 via the A/D converter 16 and the interface 4 and is converted into concentration of the specimen. The data that has been converted into the concentration is printed out via the interface 4 from the printer 17.

Then, the reaction container 6 whose photometric measurement by the multi-wavelength photometer 15 is finished is moved to the position of the cleaning mechanism 19. After the contents therein are discharged, the container is cleaned by water and supplied to the next analysis.

As described above, in the automatic analysis apparatus according to this embodiment, the specimen can be analyzed by executing sampling, reagent dispensing, agitation, photometric measurement, cleaning of the reaction container, and data processing such as concentration conversion in this order.

<Configuration of Reagent Container>

Figure 2:
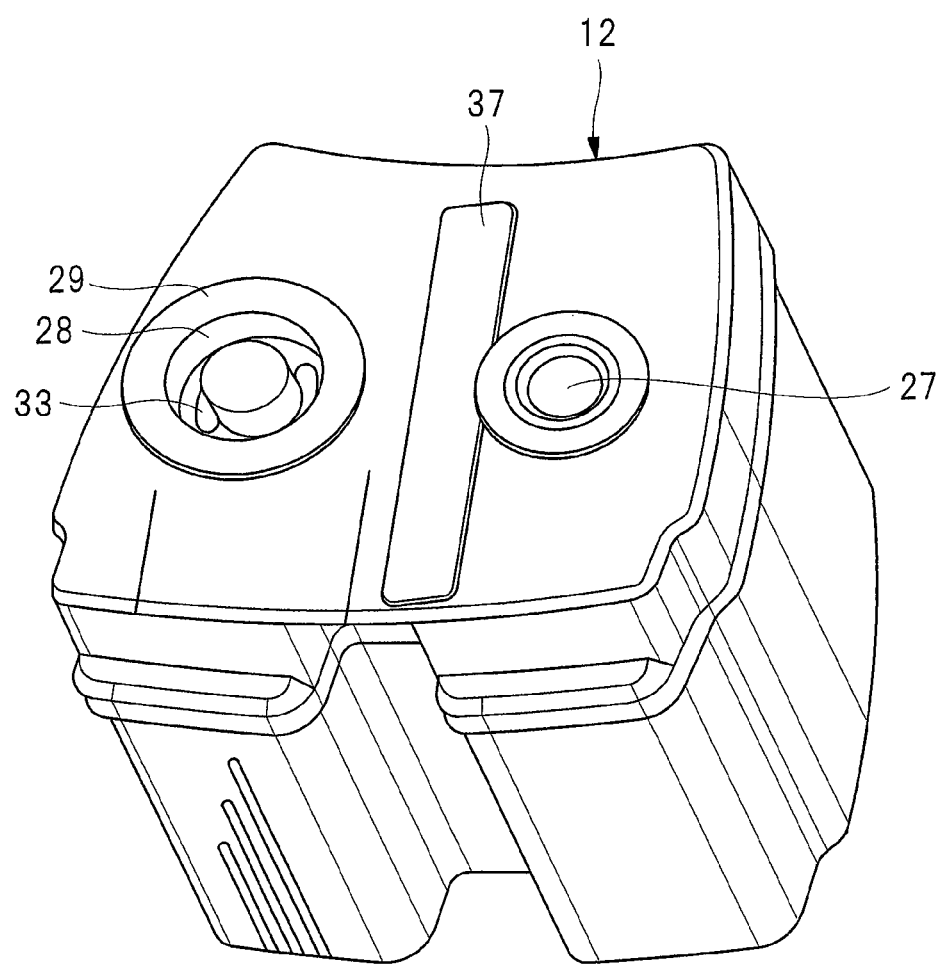
FIG. 2 is a perspective view for describing one example of a configuration of a reagent container used in the automatic analysis apparatus shown in FIG. 1.
Figure 3:
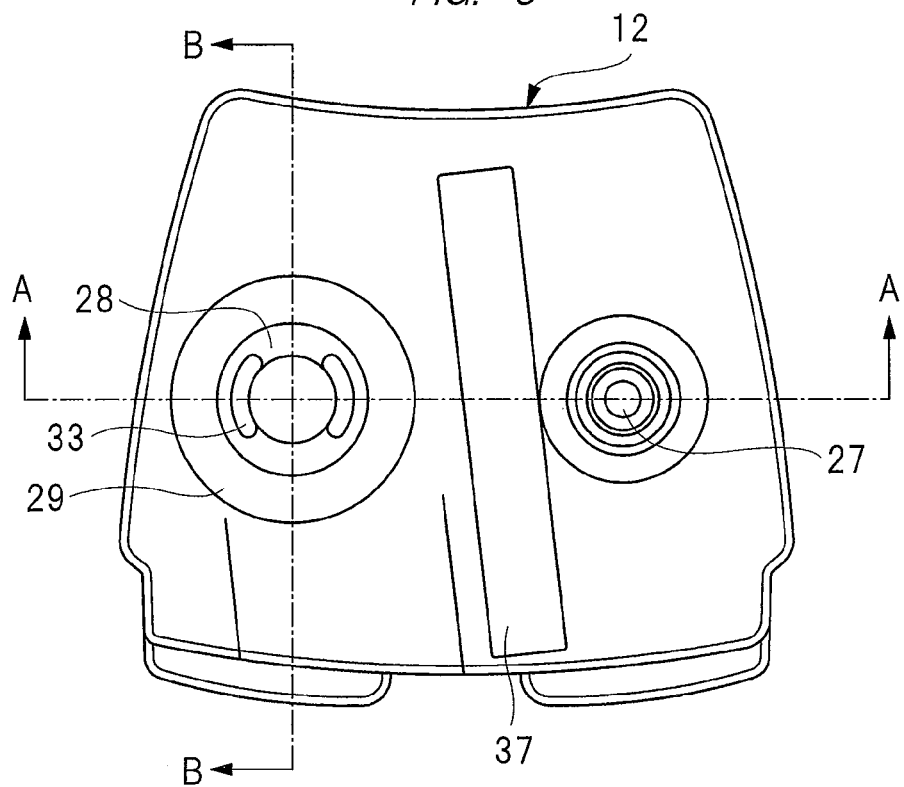
FIG. 3 is a plan view for describing one example of the reagent container shown in FIG. 2.
Figure 4:
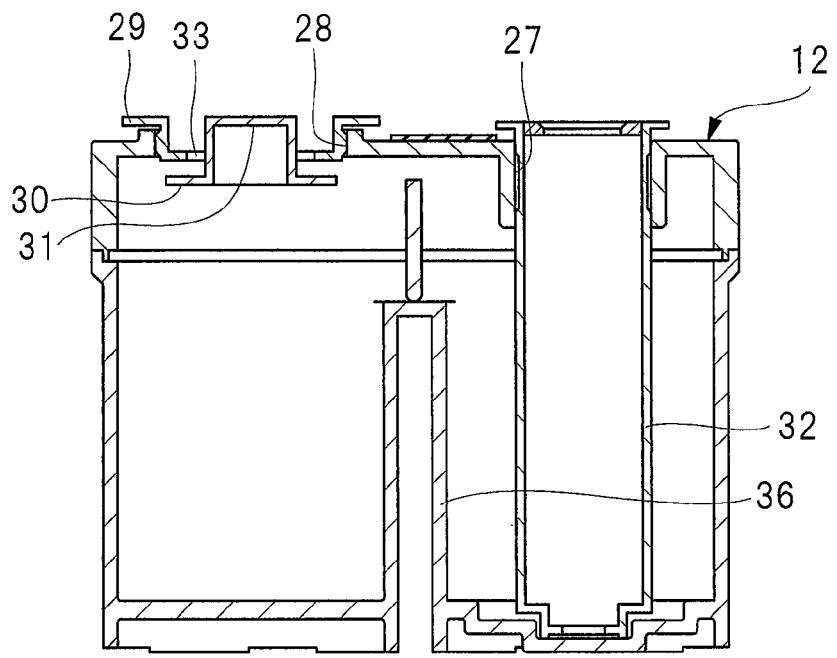
FIG. 4 is a cross-sectional view taken along the line A-A of FIG. 3.
Figure 5:
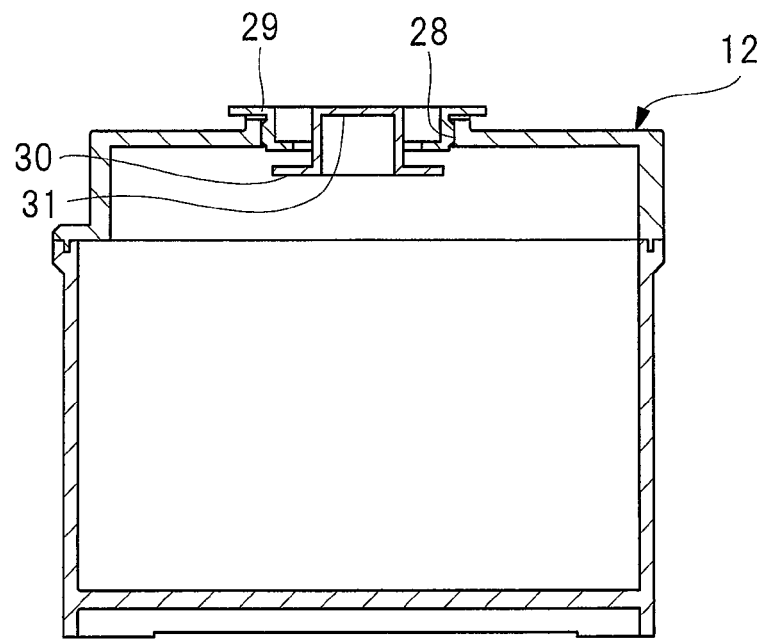
FIG. 5 is a cross-sectional view taken along the line B-B of FIG. 3.

A configuration of the reagent container 12 used in the automatic analysis apparatus shown in FIG. 1 will be described with reference to FIG. 2 to FIG. 5. FIG. 2 is a perspective view for describing one example of a configuration of the reagent container 12 used in the automatic analysis apparatus. FIG. 3 to FIG. 5 are diagrams for describing one example of the reagent container 12 shown in FIG. 2, FIG. 3 is a plan view, FIG. 4 is a cross-sectional view taken along the line A-A of FIG. 3, and FIG. 5 is a cross-sectional view taken along the line B-B of FIG. 3.

The reagent container 12 used in the automatic analysis apparatus according to this embodiment is arranged on the reagent disc 26 of the automatic analysis apparatus, and it is configured so as to be adapted for the high-speed rotation and stopping of the reagent disc 26. Since the reagent containers 12 are arranged along the circumference of the circular reagent disc 26, the shape thereof is such that a quadrangular ring is divided, and thus it is close to a box shape of a quadratic prism. Further, the reagent container 12 is configured so as to be adapted for the increase in the capacity of the reagent amount, and it has a size capable of receiving, for example, 400 ml or more of reagent.

The reagent container 12 according to this embodiment includes the first opening 27 used for sucking the reagent and the second opening 28 used for the filling of reagent. More specifically, two circular holes are opened in the reagent container 12, and the first opening 27 is a hole used for sucking the reagent from the reagent container 12 and analyzing it and the second opening 28 is a hole used for filling the reagent container 12 with the reagent. The second opening 28 is a circular hole whose diameter is larger than that of the first opening 27.

The second opening 28 is provided with the attachable/detachable lid 29. The lid 29 has the air vent 33 and the first and second shield plates 30 and 31 that prevent spattering of the reagent through the air vent 33 due to a wave motion of the reagent. More specifically, the lid 29 is provided on the second opening 28 so that the reagent does not spatter to an outside of an upper part of the reagent container 12 even when the reagent disc 26 rotates or stops at a high speed. Although details will be described later, the reagent is prevented from spattering to the outside of an upper part of the reagent container 12 by, in particular, the first shield plate 30 provided below the air vent 33 and the second shield plate 31 provided inside the air vent 33.

A wave motion preventing tube 32 for preventing a wave motion of reagent is inserted into the first opening 27. More specifically, the wave motion preventing tube 32 is inserted into the first opening 27 so that a wave motion does not occur in the reagent in the reagent container 12 even when the reagent disc 26 rotates or stops at a high speed. The wave motion preventing tube 32 has a hole for taking in the reagent in the reagent container 12, and this hole is provided at a lowermost part of the wave motion preventing tube 32.

The air vent 33 of the lid 29 attached to the second opening 28 is an opening area for making a position of a liquid surface of the reagent in the reagent container 12 flush with a liquid surface in the wave motion preventing tube 32. More specifically, the air vent 33 of the lid 29 is provided because the liquid surface of the reagent in the reagent container 12 needs to be kept constant at the suction of the reagent in a pressure relationship between the inside of the reagent container 12, the inside of the wave motion preventing tube 32, and the outside of the reagent container 12. For this season, the air vent 33 desirably has a certain area or more that is not too small. As a rough indication, the air vent desirably has an area that is the same as or not less than that of the first opening 27. When there are a plurality of air vents, a sum of the areas of the respective air vents is desirably not less than or the same as the area of the first opening 27. The same is true of the second to fifth embodiments described later.

The reagent container 12 according to this embodiment is further provided with a partition 36 between a reagent receiving part below the first opening 27 and a reagent receiving part below the second opening 28 in order to prevent the wave motion of the reagent in the reagent container 12. The partition 36 is not provided on an internal upper surface side and an internal lower surface side of the reagent container 12, and the reagent flows back and forth through the internal lower surface side.

Further, an identification label 37 of a reagent bar code in which a manufacturing lot number of reagent, a container size, an expiration date of the reagent, a sequence number and others are recorded as the reagent information is stuck to an upper surface of the reagent container 12 between the first opening 27 and the second opening 28.

<Configuration of Lid>

Figure 6:
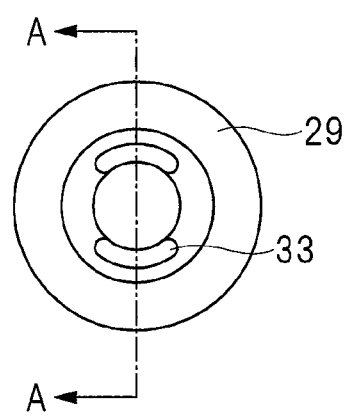
FIG. 6 is a diagram for describing one example of a configuration of a lid of the reagent container shown in FIG. 2 to FIG. 5, (a) is a plan view, and (b) is a cross-sectional view taken along the line A-A of (a)
Figure 6:
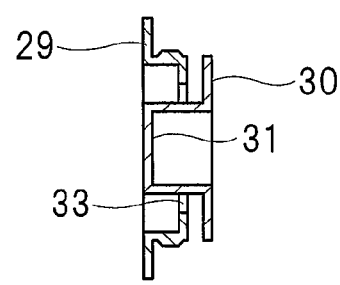

A configuration of the lid 29 of the reagent container 12 shown in FIG. 2 to FIG. 5 will be described with reference to FIG. 6. FIG. 6 is a diagram for describing one example of the configuration of the lid 29 of the reagent container 12, (a) is a plan view, and (b) is a cross-sectional view taken along the line A-A of (a).

The lid 29 of the reagent container 12 according to this embodiment is attachable to and detachable from the second opening 28 of the reagent container 12, and is provided with the air vent 33 and the first and second shield plates 30 and 31 for preventing the spattering of the reagent through the air vent 33 due to a wave motion of the reagent.

The air vent 33 of the lid 29 is formed of an elliptical (approximately close to ellipse) hole. Below the air vent 33, the first shield plate 30, whose diameter is smaller than the diameter of the second opening 28 and larger than the diameter of the air vent 33 (diameter of long axis of elliptical shape) and which functions as a shield plate for preventing the spattering of the reagent, is provided. Further, inside the air vent 33, the second shield plate 31, which has a cylindrical projection whose inner side functions as a shield plate for preventing the spattering of the reagent, is provided.

More specifically, the first shield plate 30 for preventing the spattering of the reagent is provided below the air vent 33 so that the reagent in the reagent container 12 does not spatter through the air vent 33 to the outside of the upper part of the reagent container 12 when the reagent disc 26 rotates and stops at a high speed. Further, inside the air vent 33, the inner side of the cylindrical projection functions as the second shield plate 31.

The lid 29 is configured by combining two cylindrical parts having brims on their upper surfaces and different sizes (namely, brimmed hat shapes) with one of them being upside down. The air vent 33 of an elliptical shape is opened in the bottom of the larger cylindrical part, and the bottom of the smaller cylindrical part is inserted to be fitted into the air vent 33 of the elliptical shape. Bottom and side surface portions on an inner side of the smaller cylindrical part correspond to the inner side of the cylindrical projection that functions as the second shield plate 31. Further, the brim portion of the smaller cylindrical part corresponds to the first shield plate 30.

When the lid 29 is attached to the reagent container 12, the brim portion of the larger cylindrical part comes to an upper side and the brim portion of the smaller cylindrical part comes to a lower side. The brim portion of the larger cylindrical part abuts on an upper surface of a peripheral part of the second opening 28 of the reagent container 12, and an outer peripheral part of the larger cylindrical part is fitted into an inner peripheral part of the second opening 28 of the reagent container 12.

<Comparison of Spattering of Reagent Between Reagent Container of this Embodiment and Conventional Reagent Container>

Figure 7:
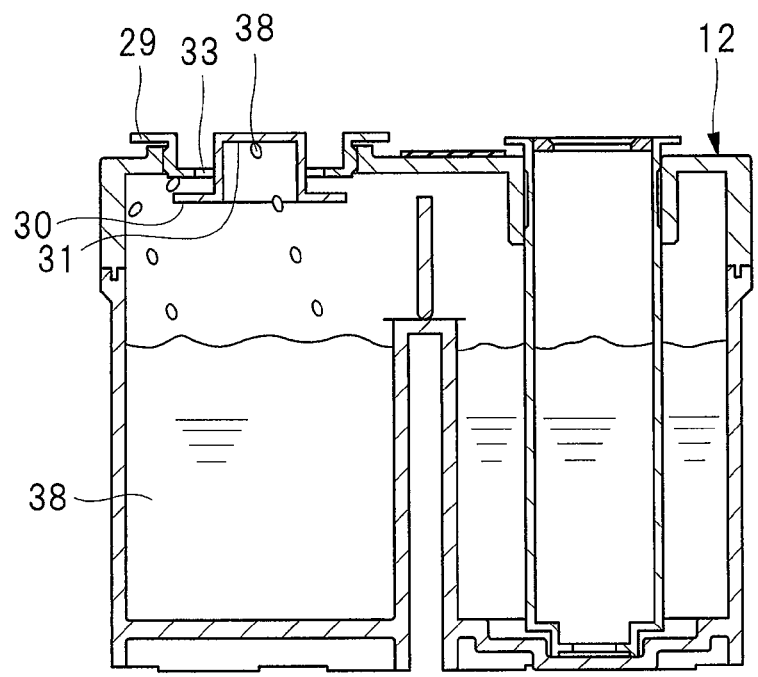
FIG. 7 is a cross-sectional view for describing one example of spattering of reagent in the reagent container according to the first embodiment of the present invention.
Figure 8:
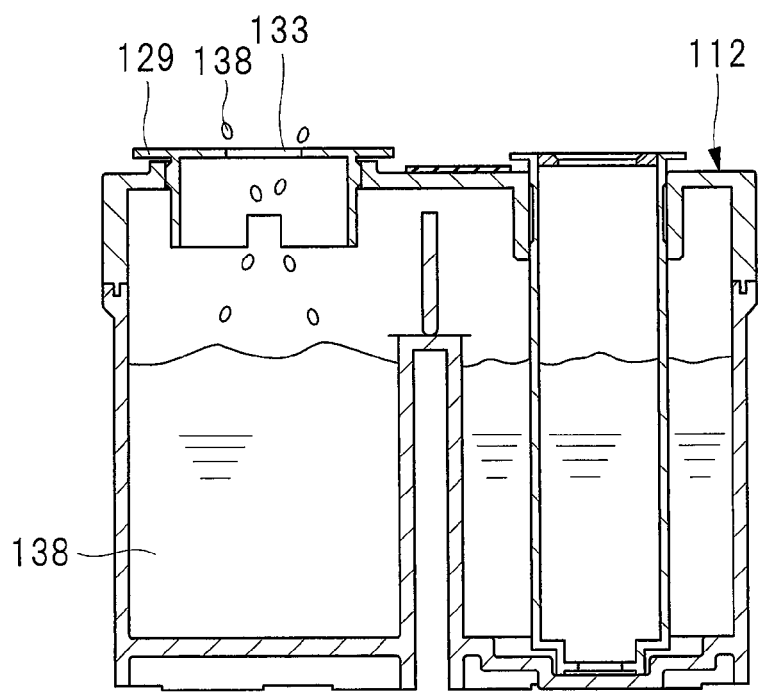
FIG. 8 is a cross-sectional view for describing one example of spattering of reagent in a conventional reagent container.

The comparison of spattering of reagent between the reagent container 12 according to this embodiment shown in FIG. 2 to FIG. 6 and the conventional reagent container will be described with reference to FIG. 7 and FIG. 8. FIG. 7 is a cross-sectional view for describing one example of the spattering of the reagent in the reagent container 12 according to this embodiment, and FIG. 8 is a cross-sectional view for describing one example of the spattering of the reagent in the conventional reagent container. These are cross-sectional views corresponding to FIG. 4 shown above.

In a conventional reagent container 112, when the reagent disc 26 rotates and stops at a high speed, reagent 138 in the reagent container 112 spatters out of the reagent container 112 in some cases as shown in FIG. 8. More specifically, in the conventional reagent container 112, since an air vent 133 is provided in an upper surface of a lid 129 but a shield plate is not provided below the air vent 133, the reagent 138 spatters to the outside through the air vent 133 in some cases.

On the contrary, in the reagent container 12 according to this embodiment, as shown in FIG. 7, the air vent 33 is provided in the lid 29, the first shield plate 30 is provided below the air vent 33 and the second shield plate 31 is provided inside the air vent 33, so that the reagent 38 can be prevented from spattering out of the reagent container 12. More specifically, when the reagent disc 26 rotates and stops at a high speed, the reagent in the reagent container 12 oscillates greatly, but the great wave motion of the reagent due to the oscillation does not cause the reagent to spatter out of the reagent container 12.

<Prevention of Spattering of Reagent in Reagent Container of this Embodiment>

Figure 9:
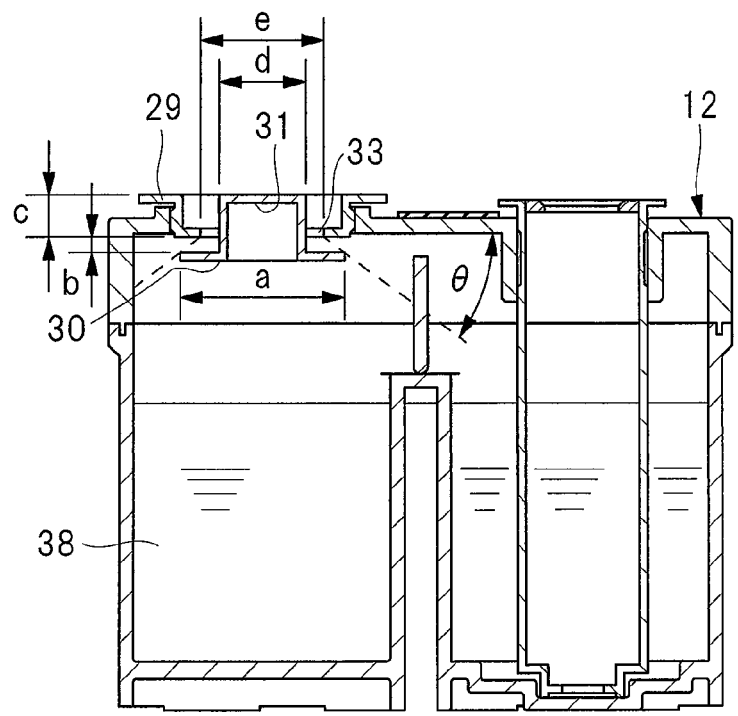
FIG. 9 is a cross-sectional view for describing one example of preventing the spattering of the reagent in the reagent container according to the first embodiment of the present invention.
Figure 10:
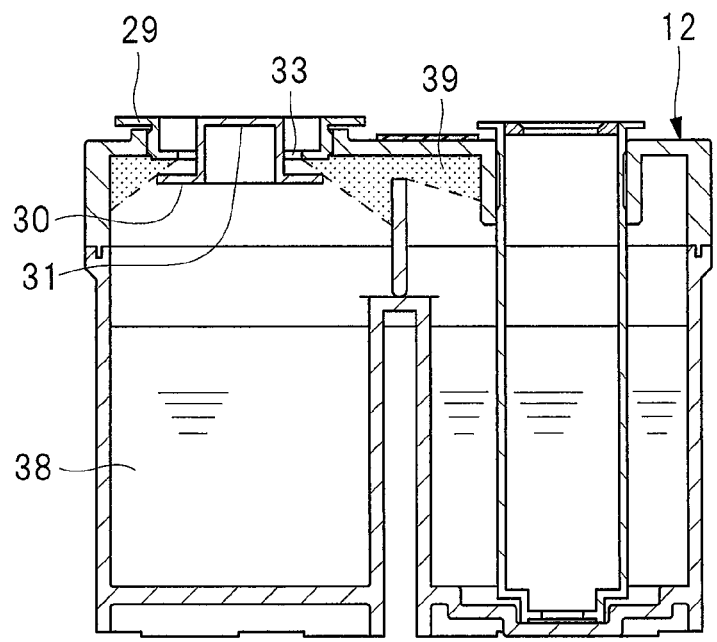
FIG. 10 is a cross-sectional view for describing one example of a range of the prevention of the spattering of the reagent in the reagent container according to the first embodiment of the present invention.

Prevention of spattering of the reagent 38 in the reagent container 12 according to this embodiment shown in FIG. 2 to FIG. 6 will be described with reference to FIG. 9 and FIG. 10. FIG. 9 is a cross-sectional view for describing one example of preventing the spattering of the reagent 38 in the reagent container 12, and FIG. 10 is a cross-sectional view for describing one example of a prevention range of the spattering of the reagent 38. These are cross-sectional views corresponding to FIG. 4 shown above.

In FIG. 9, a dimension a represents a diameter of the first shield plate 30, a dimension b represents a gap between the air vent 33 and the first shield plate 30, a dimension c represents a gap between the air vent 33 and the upper surface of the lid 29, a dimension d represents a diameter of the cylindrical projection of the second shield plate 31, and a dimension e represents an outer dimension of the air vent 33. Further, an angle $\theta$ represents an angle from an internal upper surface toward the inside of the reagent container 12 with the outside of the air vent 33 as a fulcrum.

In the case of these dimensions, in the range outside the angle indicated by a dotted portion 39 (angle $\theta$) shown in FIG. 10, the spattering out of the reagent container 12 is less likely to occur. The respective dimensions a and b may be varied within the angle of the hatched portion 39. However, the dimension a is not more than the diameter of the hole of the second opening 28 for attaching the lid 29.

Effects of First Embodiment

The automatic analysis apparatus according to this embodiment and the reagent container 12 used in the automatic analysis apparatus described above can achieve the following effects.

(1) The reagent container 12 has the first opening 27 used for sucking the reagent 38 and the second opening 28 used for the filling of the reagent 38. The second opening 28 is provided with the attachable/detachable lid 29. The lid 29 is provided with the air vent 33, the first shield plate 30 and the second shield plate 31 for preventing the spattering of the reagent 38 through the air vent 33 due to the wave motion of the reagent 38. Consequently, even when the reagent container 12 with large capacity is rotated at a high speed, the reagent 38 in the reagent container 12 can be prevented from spattering out of the reagent container 12. Therefore, stain on the identification label 37 of the reagent container 12 and stain on a window for reading the identification label 37 can be prevented. As a result, reading failure of the bar code of the identification label 37 due to the spattering of the reagent 38 can be reduced, and the automatic analysis apparatus with high reliability can be provided.

(2) The reagent container 12 has the capacity capable of receiving 400 ml or more of the reagent 38. The wave motion preventing tube 32 for preventing the wave motion of the reagent 38 is inserted into the first opening 27. The air vent 33 of the lid 29 attached to the second opening 28 is an opening area for making the position of the liquid surface of the reagent 38 in the reagent container 12 flush with the liquid surface in the wave motion preventing tube 32. As a result, even in the reagent container 12 with large capacity capable of receiving 400 ml or more of the reagent, the effect similar to above-described (1) can be achieved in the relationship in the opening area between the wave motion preventing tube 32 and the air vent 33.

(3) The air vent 33 is formed of an elliptical hole. The first shield plate 30, which has a diameter smaller than the diameter of the second opening 28 and larger than the diameter of the air vent 33 and functions as a shield plate, is provided below the air vent 33. The second shield plate 31, which has a cylindrical projection whose inner side functions as a shield plate, is provided inside the air vent 33. As a result, the effect similar to above-described (1) can be achieved also in a positional relationship between the air vent 33, the first shield plate 30 and the second shield plate 31.

Second Embodiment

An automatic analysis apparatus using a reagent container according to the second embodiment will be described with reference to FIG. 11. In comparison with the first embodiment, this embodiment is different in the shape of the upper surface of the reagent container, and is characterized by providing a concave portion at a part near the lid to be gripped at the time of removing the lid. This is a configuration for facilitating the removal of the lid. The point different from the first embodiment will be mainly described below.

Figure 11:
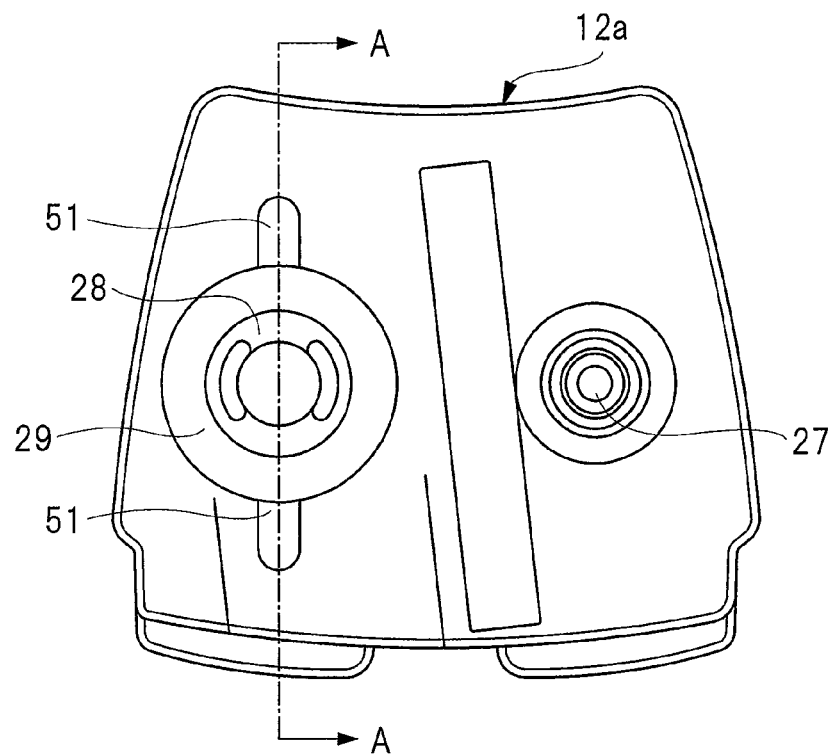
FIG. 11 is a diagram for describing one example of a configuration of a reagent container used in an automatic analysis apparatus according to the second embodiment of the present invention, (a) is a plan view, and (b) is a cross-sectional view taken along the line A-A of (a)
Figure 11:
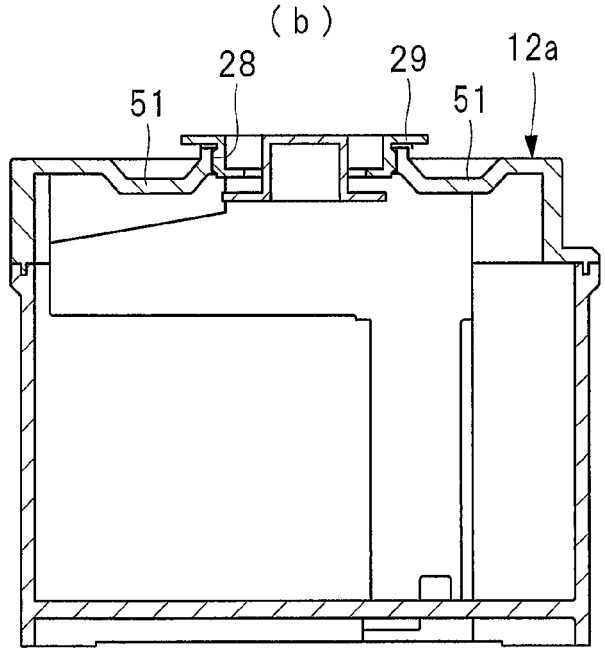

FIG. 11 is a diagram for describing one example of a configuration of a reagent container used in the automatic analysis apparatus (FIG. 1) similar to that in the first embodiment, (a) is a plan view, and (b) is a cross-sectional view taken along the line A-A of (a).

In a reagent container 12a used in the automatic analysis apparatus according to this embodiment, concave portions 51 concaved in the upper surface of the reagent container 12a are provided at two positions touched by fingers so that the lid 29 can be easily removed when filling the reagent container 12a with reagent. The concave portions 51 are provided at the two positions in a peripheral part of the second opening 28 in a direction approximately vertical to a line connecting the second opening 28 and the first opening 27. Note that positions to dispose the concave portions 51 are not limited to these.

Consequently, in the reagent container 12a used in the automatic analysis apparatus according to this embodiment, as the effect different from the effects in the first embodiment, since the concave portions 51 are provided at the positions near the lid 29 to be gripped by the fingers, the lid 29 can be easily removed from the reagent container 12a.

Third Embodiment

An automatic analysis apparatus using a reagent container according to the third embodiment will be described with reference to FIG. 12. In comparison with the first embodiment, this embodiment is different in the shape of a lid used for a reagent container, and is characterized in that a surface of the lid in which an air vent is disposed has a slope structure so that reagent adhered to the surface drops down through the air vent. This is the structure in which the reagent adhered to the lid is made to drop into the reagent container. The point different from the first embodiment will be mainly described below.

Figure 12:
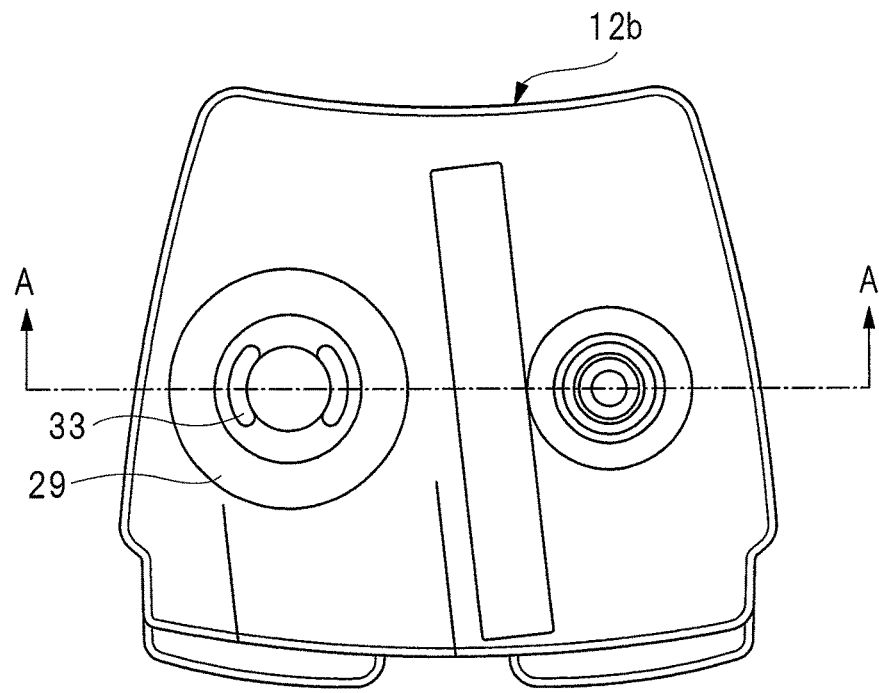
FIG. 12 is a diagram for describing one example of a configuration of a reagent container used in an automatic analysis apparatus according to the third embodiment of the present invention, (a) is a plan view, and (b) is a cross-sectional view taken along the line A-A of (a)
Figure 12:
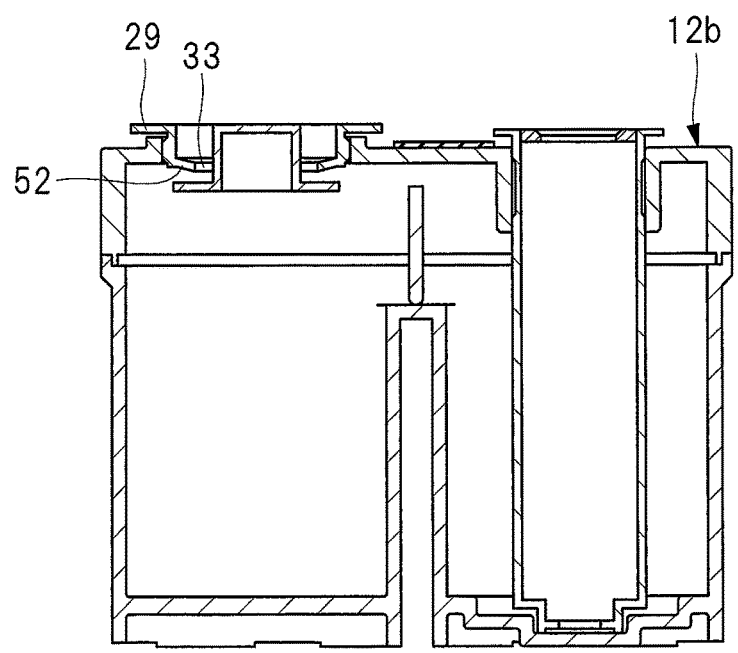

FIG. 12 is a diagram for describing one example of a configuration of a reagent container used in the automatic analysis apparatus (FIG. 1) similar to that in the first embodiment, (a) is a plan view, and (b) is a cross-sectional view taken along the line A-A of (a).

In a reagent container 12b used in the automatic analysis apparatus according to this embodiment, a slope portion 52 is provided so that even when reagent in the reagent container 12b spatters upward and adheres to a surface of the lid 29 having the air vent 33 at the time of high-speed rotation and stopping of the reagent disc 26, the reagent drops down through the air vent 33. The slope portion 52 extends down toward the inside of the reagent container 12b from a periphery to a center of the lid 29.

Consequently, in the reagent container 12b used in the automatic analysis apparatus according to this embodiment, as the effect different from the effects in the first embodiment, even when the reagent spatters upward and adheres to the lid 29, the reagent can be made to drop into the reagent container 12b along the slope of the slope portion 52.

Fourth Embodiment

An automatic analysis apparatus using a reagent container according to the fourth embodiment will be described with reference to FIG. 13 to FIG. 16. In comparison with the first embodiment, this embodiment is characterized by four types of lids of the reagent container each having different shapes. The point different from the first embodiment will be mainly described below.

FIG. 13 to FIG. 16 are diagrams for describing examples of a configuration of a lid of the reagent container used in the automatic analysis apparatus (FIG. 1) similar to that in the first embodiment, and (a) is a plan view and (b) is a cross-sectional view taken along the line A-A of (a) in each of FIG. 13 to FIG. 16.

Figure 13:
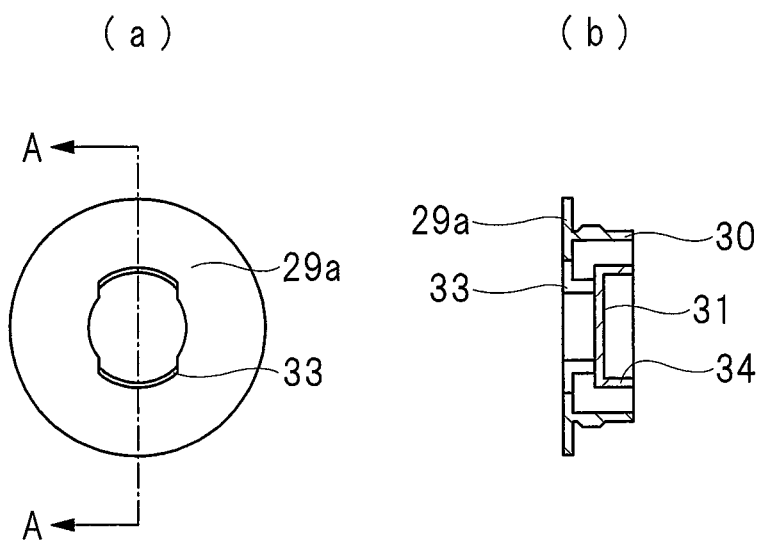
FIG. 13 is a diagram for describing one example (Example 1) of a configuration of a lid of a reagent container used in an automatic analysis apparatus according to the fourth embodiment of the present invention, (a) is a plan view, and (b) is a cross-sectional view taken along the line A-A of (a)

A lid 29a shown in FIG. 13 has the air vent 33 on its side surface, a first shield plate 30, a second shield plate 31, and a third shield plate 34. More specifically, the lid 29a is configured by combining a larger bottomless cylindrical part with a brim and a smaller cylindrical part. The air vent 33 is provided at a connection part between the larger cylindrical part and the smaller cylindrical part. A side surface portion of the larger cylindrical part functions as the first shield plate 30, a bottom portion of the smaller cylindrical part functions as the second shield plate 31, and a side surface portion of the smaller cylindrical part functions as the third shield plate 34. Further, a height of a projection of the smaller cylindrical part is lower than an upper surface of the lid 29.

Figure 14:
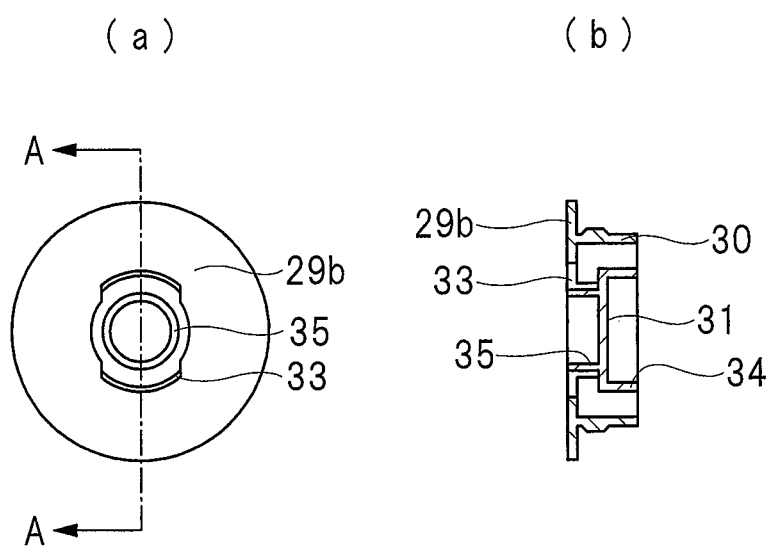
FIG. 14 is a diagram for describing one example (Example 2) of a configuration of the lid of the reagent container used in the automatic analysis apparatus according to the fourth embodiment of the present invention, (a) is a plan view, and (b) is a cross-sectional view taken along the line A-A of (a)

A lid 29b shown in FIG. 14 has a fourth shield plate 35 in addition to the configuration in FIG. 13. More specifically, the lid 29b is configured by joining a still smaller bottomless cylindrical part to an outer bottom portion of the smaller cylindrical part. A side surface portion of the still smaller cylindrical part functions as the fourth shield plate 35.

Figure 15:
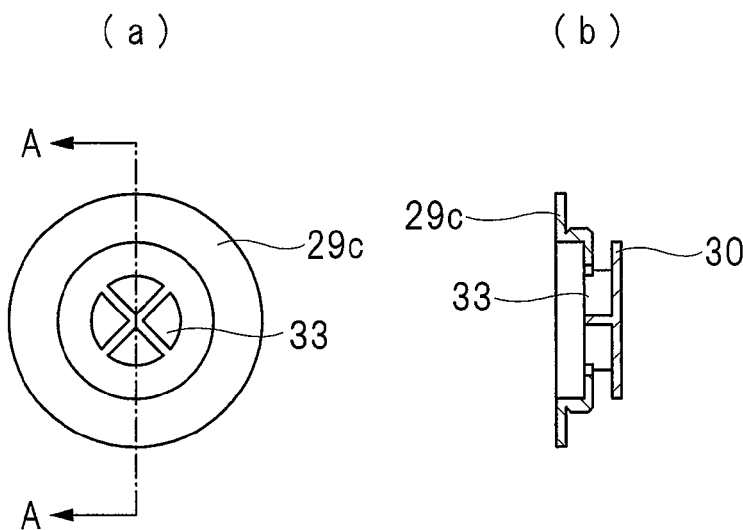
FIG. 15 is a diagram for describing one example (Example 3) of a configuration of the lid of the reagent container used in the automatic analysis apparatus according to the fourth embodiment of the present invention, (a) is a plan view, and (b) is a cross-sectional view taken along the line A-A of (a)

A lid 29c shown in FIG. 15 has four air vents 33 each having a fan-like shape and the first shield plate 30. More specifically, the lid 29c is configured by joining a partially bottomless cylindrical part with a brim and a circular plate part slightly smaller than a bottom part of the cylindrical part at their center portions. The four air vents 33 in a fan-like shape are provided at the bottom portion of the cylindrical part with a brim. The circular plate shaped portion functions as the first shield plate 30.

A lid 29d shown in FIG. 16 has the second shield plate 31 in addition to the configuration in FIG. 15. More specifically, the lid 29d is configured by joining a still smaller bottomless cylindrical part to an inner bottom portion of the cylindrical part. A side surface portion of the still smaller cylindrical part functions as the second shield plate 31.

As described above, in the lids 29a to 29d of the reagent container 12 used in the automatic analysis apparatus according to this embodiment, as the effect different from the effects in the first embodiment, the lids 29a to 29d of the reagent container 12 can have various shapes in addition to the shape described in the first embodiment. For example, the shapes may be changed in accordance with the type and capacity of reagent to be filled into the reagent container 12.

Fifth Embodiment

An automatic analysis apparatus using a reagent container according to the fifth embodiment will be described with reference to FIG. 17. In comparison with the first embodiment, this embodiment is characterized in that the reagent container has a shape obtained by combining a plurality of reagent containers. The point different from the first embodiment will be mainly described below.

FIG. 17 is a plan view for describing one example of a configuration of the reagent container used in the automatic analysis apparatus (FIG. 1) similar to that in the first embodiment.

A reagent container 12c used in the automatic analysis apparatus according to this embodiment has a shape obtained by combining one or a plurality of containers in accordance with the purpose, and it is provided with three first openings 27 for inserting a nozzle of the reagent dispensing probe 8 into the reagent container 12c and one second opening 28 used for the filling of reagent. The above-described (FIG. 6, FIG. 13 to FIG. 16) various types of lids can be used also for the second opening 28.

Consequently, in the reagent container 12c used in the automatic analysis apparatus according to this embodiment, as the effect different from the effects in the first embodiment, the reagent container 12c having the shape obtained by combining a plurality of containers can be used in accordance with the purpose of the reagent container 12c.

In the foregoing, the invention made by the inventors of the present invention has been concretely described based on the embodiments. However, it is needless to say that the present invention is not limited to the foregoing embodiments and various modifications and alterations can be made within the scope of the present invention. For example, the embodiments above have been described in detail so as to make the present invention easily understood, and the present invention is not limited to the embodiment having all of the described constituent elements. Also, a part of the configuration of one embodiment may be replaced with the configuration of another embodiment, and the configuration of one embodiment may be added to the configuration of another embodiment. Furthermore, another configuration may be added to a part of the configuration of each embodiment, and a part of the configuration of each embodiment may be eliminated or replaced with another configuration.

EXPLANATION OF REFERENCE CHARACTERS

1: specimen container, 2: specimen disc, 3: computer, 4: interface, 5: specimen dispensing probe, 6: reaction container, 7: specimen pump, 8: reagent dispensing probe, 9: reaction tank, 11: reagent pump, 12, 12a, 12b, 12c: reagent container, 13: agitating mechanism, 15: multi-wavelength photometer, 16: A/D converter, 17: printer, 18: CRT, 19: cleaning mechanism, 20: cleaning mechanism vacuum pump, 21: keyboard, 23: reagent bar code reading device, 25: hard disc, 26: reagent disc, 27: first opening, 28: second opening, 29, 29a, 29b, 29c, 29d: lid, 30: first shield plate, 31: second shield plate, 32: wave motion preventing tube, 33: air vent, 34: third shield plate, 35: fourth shield plate, 36: partition, 37: identification label, 38: reagent, 39: dotted portion, 51: concave portion, 52: slope portion, 112: reagent container, 129: lid, 133: air vent, 138: reagent

The invention claimed is:

1. A reagent container for an automatic analysis apparatus comprising:
a first opening used for sucking reagent;
a second opening used for filling the reagent container with the reagent;
a lid which is detachably attached in the second opening;
wherein the lid includes an air vent, a first shield plate disposed below the air vent, and a second shield plate disposed above and inside the air vent,
wherein the air vent is disposed a first distance below an upper surface of the lid,
wherein the first shield plate projects into an interior of the reagent container below the air vent and the first shield plate is separated from the air vent by a second distance,
wherein a first diameter of the first shield plate is less than a second diameter of the second opening, and
wherein the first shield plate restricts spattering of the reagent from the interior of the reagent container through the air vent due to a wave motion of the reagent.

2. The reagent container according to claim 1,
wherein the air vent is a hole having an area that is equal to or greater than an area of the first opening.

3. The reagent container according to claim 1, further comprising:
a wave motion preventing tube for preventing the wave motion of the reagent is inserted into the first opening,
wherein the reagent container has a capacity of 400 ml or more, and
wherein the air vent of the lid attached to the second opening is an opening area which fixes communication between an exterior and the interior of the reagent container thereby making a position of a liquid surface of the reagent in the reagent container flush with a liquid surface in the wave motion preventing tube.

4. The reagent container according to claim 3,
wherein the air vent is an elliptical hole,
wherein the first diameter of the first shield plate is larger than a diameter of the air vent, and
wherein the first diameter of the first shield plate is greater than a third diameter of the second shield plate having a cylindrical shape, and
wherein the air vent is provided outside the second shield plate.

5. The reagent container according to claim 4,
wherein the reagent container includes a concave portion at a position next to the lid to be gripped at a time of removing the lid.

6. The reagent container according to claim 4,
wherein an upper surface of the lid projects above the cylindrical projection of the second shield plate.

7. The reagent container according to claim 4,
wherein a surface of the lid in which the air vent is disposed has a slope structure which is provided outside of the air vent and slopes towards the air vent so that the reagent drops down through the air vent when the reagent adheres to the surface.

8. An automatic analysis apparatus, comprising:
a reagent disc on which a plurality of reagent containers are placed;
a tank on which a reaction container including a specimen to be analyzed is placed;
a reagent dispensing probe to suck a reagent from one of the reagent containers on the reagent disc and dispense the reagent into the reaction container; and a photometer to measure a reaction of the specimen and the reagent in the reaction container,
wherein each of the reagent containers includes:
a first opening used for sucking reagent;
a second opening used for filling the reagent container with the reagent;
a lid which is detachably attached in the second opening;
wherein the lid includes an air vent, a first shield plate disposed below the air vent, and a second shield plate disposed above and inside the air vent,
wherein the air vent is disposed a first distance below an upper surface of the lid,
wherein the first shield plate projects into an interior of the reagent container below the air vent and the first shield plate is separated from the air vent by a second distance,
wherein a first diameter of the first shield plate is less than a second diameter of the second opening, and
wherein the first shield plate restricts spattering of the reagent from the interior of the reagent container through the air vent due to a wave motion of the reagent.

9. The reagent container according to claim 1, wherein the second distance defines a gap which is maintained between the first shield plate and the air vent.

* * * * *